United States Patent [19]

Lix

[11] Patent Number: 5,474,058
[45] Date of Patent: Dec. 12, 1995

[54] MDI VENTILATOR DISPENSER WITH BI-DIRECTIONAL NOZZLE

[75] Inventor: Joseph N. Lix, Tucson, Ariz.

[73] Assignee: Thayer Medical Corporation, Tucson, Ariz.

[21] Appl. No.: 347,046

[22] Filed: Nov. 30, 1994

[51] Int. Cl.$^6$ .................................................. A61M 11/00
[52] U.S. Cl. .............................. 128/200.18; 128/200.14; 128/200.23
[58] Field of Search ................... 128/200.23, 200.18, 128/203.12, 203.25, 205.11, 203.23, 203.15, 203.21, 203.24, 200.21, 200.14; 222/402.2, 402.14; 239/545, 429, 8, 548, 373, 337, 338

[56] References Cited

U.S. PATENT DOCUMENTS

| | | | |
|---|---|---|---|
| 4,470,412 | 9/1984 | Nowacki et al. | 128/200 |
| 4,484,577 | 11/1984 | Sackner et al. | 128/203 |
| 4,790,305 | 12/1988 | Zoltan et al. | 128/200 |
| 5,012,803 | 5/1991 | Foley et al. | 128/200 |
| 5,178,138 | 1/1993 | Walstrom et al. | 128/200 |

Primary Examiner—Edgar S. Burr
Assistant Examiner—V. Srivastava
Attorney, Agent, or Firm—Cahill, Sutton & Thomas

[57] ABSTRACT

A dispenser for medication from an MDI canister is connected into an inspiratory stream from a ventilator to the lungs of an intubated patient. The MDI canister valve is actuated so as to deliver a stream of medication-containing liquid propellant through a medication nozzle from which the liquid is simultaneously ejected in upstream and downstream directions through upstream and downstream exit ports, respectively. The two ejected streams of medication-containing liquid form expanding upstream and downstream plumes of rapidly evaporating medication-containing droplets. The upstream and downstream exit ports of the medication nozzle are sized such that few evaporating droplets of the expanding plumes reach the inner wall of the inspiratory path before they entirely evaporate. Therefore, a high percentage of medication particles become dry and are carried by the inspiratory air stream and efficiently delivered into the lungs of the patient.

6 Claims, 1 Drawing Sheet

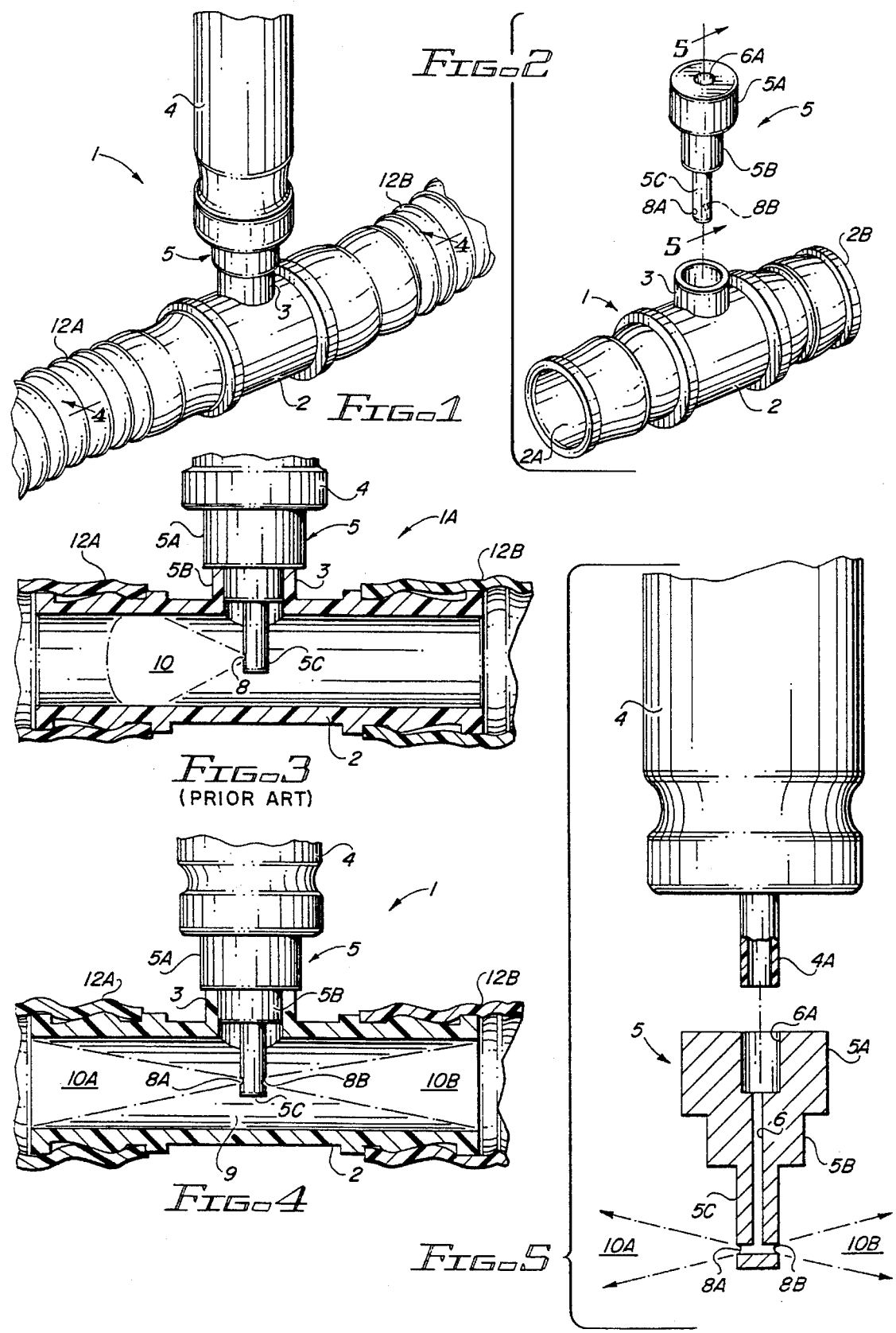

5,474,058

MDI VENTILATOR DISPENSER WITH BI-DIRECTIONAL NOZZLE

BACKGROUND OF THE INVENTION

The invention relates to devices and methods for dispensing a drug from a Metered Dose Inhaler (MDI) canister into a stream of air supplied through the inspiratory path between a ventilator and an endotracheal tube in the bronchial passage of a patient.

Drugs dispensed from metered dose inhalers usually consist of very finely divided particles, typically in the one to eight micron range. The medication particles are suspended in pressurized liquid Freon propellant which is under pressure in the MDI canister. Upon actuation, a metered dose of the drug and Freon propellant is ejected through the outlet tube of the canister and a medication nozzle of a MDI ventilation dispenser 1A as shown in FIG. 3. As the mixture of drug and Freon propellant is ejected from an exit port 8 of the medication nozzle 5 into the body 2 of MDI ventilation dispenser 1A, it is accelerated to such high velocity that shear forces with the nearly stationary ambient air cause the propellant to break up into many small, rapidly evaporating droplets, each of which contains hundreds or thousands of drug particles. The exit port 8 of a ventilation dispenser 1A (prior art FIG. 3) typically has a diameter of approximately 0.6 millimeters. The rapid evaporation of Freon droplets produces rapid cooling, which may result in condensation of water that replaces the evaporating Freon, resulting in some medication particles being contained in water droplets. In any case, the rapidly evaporating droplets travel at high speed and expand into a plume 10 along a longitudinal axis of MDI ventilation dispenser 1A. The size and maximum diameter of the plume is determined by when the droplets become completely evaporated.

Therefore, the rate at which the droplets of propellant can evaporate (thereby releasing dry particles of the drug which can be carried by the inspiratory air stream flowing through the inspiratory tubing, a wye connector, and the endotracheal tube into the lungs of the patient) is limited by how fast heat can be absorbed by the droplets from the surrounding air and the wall of the inspiratory path. (Note that evaporation is a phase transition that requires absorption of heat which must come from the droplets, which cool very quickly and therefore must absorb heat from the surrounding air for evaporation to continue.)

As is well known, a major problem with MDI ventilator dispensers is that the expanding plume 10 of large unevaporated droplets and the medication particles contained therein impinge against the inside walls of the connecting tubing that constitutes the inspiratory path. Most or all of the drug particles contained in each impinging droplet adhere to the wall of the inspiratory tubing and therefore are not carried by the inspiratory air stream into the lungs of the patient. To prevent droplets of plume 10 from impinging on the inner walls of the inspiratory path, devices called "spacers" sometimes are used. Such spacers have enlarged diameters into which the plume can continue to expand until all of the medication-containing droplets have evaporated, as described in U.S. Pat. Nos. 4,470,412 (Nowaki), 4,484,577 (Sackner), 4,790,305 (Zoltan), and 5,012,803 (Foley). Unfortunately, use of such spawcers increases the volume of the inspiratory circuit and therefore also increases the "compressibility" of the ventilator circuit.

This is undesirable because compression of air in the inspiratory circuit, as the ventilator pushes a "breath" of air into the lungs of the patient, results in a reduction in the amount of air actually delivered to the lungs of the patient. Such compression also can result in a reduction in the amount of medication delivered via the inspiratory air stream into the lungs of the patient. Thus, such compression can produce uncertainty both in the amount of oxygen and the amount of medication received by the lungs of the patient, especially if the patient happens to be a small child.

Furthermore, use of spacers also increases the amount of surface area in the inspiratory circuit on which condensation can occur, increasing the amount of condensate that accumulates and which must be drained. The expense of using spacers and the discomfort to the patient of additional weight in the apparatus connected to the end of the tracheal tube also are factors that favor avoiding the use of spacers.

Thus, there is an unmet need for an improved device and technique to reduce or eliminate the loss of medication particles contained in Freon or water droplets which impinge upon the inner surfaces of the inspiratory path.

SUMMARY OF THE INVENTION

Accordingly, it is an object of the invention to provide improved delivery of medication from an MDI canister to the lungs of a patient assisted by a ventilator.

It is another object of the invention to provide an improved MDI ventilation dispenser and method which avoids loss of medication particles through impingement of droplets containing the particles on the inner wall of the inspiratory path.

It is another object of the invention to provide an improved MDI ventilation dispenser and method which provides high efficiency of delivering medication from an MDI canister to the lungs of a patient without substantially increasing the diameter of a part of the inspiratory path, for example, by using a spacer.

Briefly described, and in accordance with one embodiment thereof, the invention provides an MDI ventilator dispenser and method for dispensing medication from an MDI canister connected into an inspiratory air stream flowing from a ventilator through inspiratory tubing and an endotracheal tube to the lungs of a patient. The MDI canister valve is actuated so as to deliver a stream of medication-containing liquid propellant through a medication nozzle from which it is simultaneously ejected through upstream and downstream exit ports in opposed upstream and downstream directions, respectively, along a longitudinal axis of the MDI ventilator dispenser. The two ejected streams of medication-containing liquid form expanding upstream and downstream plumes of rapidly evaporating medication-containing droplets. The upstream and downstream exit ports of the medication nozzle are sized such that the expanding plumes of rapidly evaporating droplets are smaller, and fewer medication-containing droplets can reach the inner wall of the inspiratory path before they entirely evaporate. Therefore, a high percentage of medication particles become essentially dry and are carried by the inspiratory air stream and efficiently delivered into the lungs of the patient.

BRIEF DESCRIPTION OF THE DRAWINGS

FIG. 1 is a perspective view of the MDI ventilator dispenser of the present invention connected to sections of inspiratory hose connecting a ventilator to an intubated patient.

FIG. 2 is a perspective exploded view of the MDI ventilator dispenser of the present invention.

FIG. 3 is a section view of a prior art MDI ventilator dispenser.

FIG. 4 is a section view along section line 4—4 of FIG. 1.

FIG. 5 is a detailed partial section view of the medication nozzle included in FIG. 4.

DETAILED DESCRIPTION OF THE PREFERRED EMBODIMENT

Referring to FIGS. 1, 2, 4, and 5, MDI ventilation dispenser 1 includes a cylindrical plastic body or T-coupler 2 having a passage 9 between a downstream outlet port 2A and an upstream inlet port 2B. A nozzle port or transverse port 3 is provided as part of T-coupler 2 and is perpendicular to the longitudinal axis of body 2. A medication nozzle 5 is cemented into nozzle port 3. An MDI canister 4 has its stem 4A (FIG. 5) inserted into a receiving hole 6A in the upper portion of medication nozzle 5. Receiving hole 6A is continuous with a channel 6 that extends through a cylindrical shoulder 5B and a stem 5C of medication nozzle 5 to both a downstream exit port 8A and an upstream exit port 8B at the lower end portion of medication nozzle stem 5C. Both downstream exit port 8A and upstream exit port 8B are aligned with the longitudinal axis of T-coupler 2.

Thus, the structure shown in FIGS. 1, 2, 4 and 5 is similar to that of the prior art MDI ventilator dispenser shown in FIG. 3 except that medication nozzle 5 contains two, rather than one, axially opposed exit ports 8A and 8B on opposite sides of medication nozzle stem 5C.

When MDI canister 4 is depressed so as to actuate its outlet valve, a downstream plume 10A and an upstream plume 10B of rapidly evaporating medication-containing droplets are simultaneously ejected from exit ports 8A and 8B, respectively, as shown in FIGS. 4 and 5. The air stream (which typically is oxygen-enriched) from a ventilator (not shown) flows through standard large bore 22 millimeter tubing section 12B into inlet port 2B and through passage 9, carrying dry medication particles which have been released by evaporation of Freon propellent droplets and/or water droplets, out of downstream port 2A and ventilator tubing 12A to an endotracheal tube intubated in a patient.

In accordance with the present invention, the total area of the two exit ports 8A and 8B in FIG. 3 is equal to the area of the single exit port 8 in the prior art device of FIG. 3, so the diameter of each of exit ports 8A and 8B of the present invention is approximately 0.4 millimeters. Consequently, only half as much medication-containing Freon is ejected from each of exit ports 8A and 8B as is the case for the prior art device of FIG. 3, and therefore upstream plume 10B and downstream plume 10A in FIGS. 1, 2, 4 and 5 are smaller and expand at smaller cone angles than is the case for the single plume 10 ejected by the prior art device of FIG. 3. Consequently, more of the medication-containing droplets in plumes 10A and 10B evaporate before they impinge on the inner wall of the inspiratory path. Therefore, more of the medication particles are released into the inspiratory air stream as the droplets evaporate and are carried by the inspiratory air stream through the endotracheal tube into the lungs of the patient.

The operation of MDI ventilator dispenser 1 of the present invention was compared with the operation of the prior art ventilation dispenser 1A of FIG. 3 by connecting each in the inspiratory path of a testing assembly including a Puritan-Bennett MA-1 ventilator adjusted to deliver air at an inspiratory flow rate of 45 liters per minute through an 8.5 millimeter endotracheal tube. The ventilator was set to deliver breaths at five-second intervals at 800 cubic centimeters per breath. A Ventolin MDI canister 4 was automatically actuated at the start of inspiration of every third breath produced by the ventilator. The inspiratory path included eight feet of the standard large-bore 22 millimeter tubing, the MDI ventilator dispenser (1 or 1A), one foot of 22 millimeter tubing 12A, a typical wye connector, an elbow, and an 8.5 millimeter endotracheal tube. A collection filter (a Baxter two-way nonconductor anesthesia filter Catalog No. 43410241) was attached to the distal end of the endotracheal tube.

The procedure for collecting medication particles from the inspiratory air stream was as follows. The MDI canister 4 was shaken and actuated once before inserting it into the automatic actuator, which then was allowed to deliver five metered doses of Ventolin from the MDI canister. The filter then was removed, and 10 milliliters of buffer solvent were delivered by a pipette into the filter. The buffer solvent consisted of 0.25 M of HCl and 0.5 M of $KH_2PO_4$. The liquid absorbance was measured by means of a spectral analyzer at a wave length of 275 nanometers. The absorbance of a reference standard solution in the same buffer solvent was measured concurrently, and the amount of medication delivered to the filter then was determined by referring to a standard reference working curve.

The results of the foregoing are shown in Table 1.

TABLE 1

| Description | Temp (degree) | % Rel hum | Absorbance @ 275 nm | # of Doses | Solvent volume (ml) | Micrograms per dose |
|---|---|---|---|---|---|---|
| 34 BI | 73 | 53 | 0.121 | 5 | 10.00 | 44.4 |
| 26 BI | 75 | 52 | 0.125 | 5 | 10.00 | 45.9 |
| 38 BI | 73 | 51 | 0.133 | 5 | 10.00 | 48.8 |
| 30 BI | 75 | 46 | 0.134 | 5 | 10.00 | 49.2 |
| 6 BI | 75 | 49 | 0.135 | 5 | 10.00 | 49.5 |
| 2 BI | 75 | 50 | 0.135 | 5 | 10.00 | 49.5 |
| 14 BI | 76 | 53 | 0.142 | 5 | 10.00 | 52.1 |
| 18 BI | 76 | 52 | 0.153 | 5 | 10.00 | 56.1 |
| 10 BI | 75 | 52 | 0.154 | 5 | 10.00 | 56.5 |
| 28 SINGLE | 74 | 49 | 0.045 | 5 | 10.00 | 16.5 |
| 4 SINGLE | 76 | 46 | 0.055 | 5 | 10.00 | 20.2 |
| 24 SINGLE | 74 | 47 | 0.058 | 5 | 10.00 | 21.3 |
| 20 SINGLE | 76 | 52 | 0.062 | 5 | 10.00 | 22.7 |
| 16 SINGLE | 75 | 52 | 0.069 | 5 | 10.00 | 25.3 |
| 8 SINGLE | 76 | 47 | 0.07 | 5 | 10.00 | 25.7 |

TABLE 1-continued

| Description | Temp (degree) | % Rel hum | Absorbance @ 275 nm | # of Doses | Solvent volume (ml) | Micrograms per dose |
| --- | --- | --- | --- | --- | --- | --- |
| 40 SINGLE | 73 | 54 | 0.074 | 5 | 10.00 | 27.1 |
| 12 SINGLE | 73 | 54 | 0.076 | 5 | 10.00 | 27.9 |
| 32 SINGLE | 74 | 52 | 0.081 | 5 | 10.00 | 29.7 |
| 36 SINGLE | 73 | 50 | 0.085 | 5 | 10.00 | 31.2 |

The results were that the MDI ventilator dispenser 1 of the present invention delivered almost twice the amount of medication into the filter as the prior art MDI ventilator dispenser 1A. Therefore, nearly twice as much medication would have been delivered to the lungs of a patient by the present invention as by the prior art device. Consequently, fewer doses of medication are needed when the present invention is used, and this results in savings in the cost of treatment and the amount of time required for treatment.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention. For example, MDI port 5 could be formed as part of a spacer, such that one or both of the upstream plume and the downstream plume expand into the spacer.

What is claimed is:

1. A device for dispersing medication from an MDI canister into an inspiratory path between a ventilator and an endotracheal tube, comprising in combination:
   (a) a body having a passage extending between an inlet port and an outlet port, the inlet port and outlet port being adapted to couple the body into the inspiratory path;
   (b) a nozzle port opening into a midportion of the body;
   (c) a medication nozzle disposed in the nozzle port for dispensing aerosol medication from an MDI canister into the body, the medication nozzle including a head portion connected in sealed relation to the nozzle port and a stem portion having a receiving opening for receiving an output stem of an MDI canister, the stem portion being attached to the head portion, a channel extending through stem portion from the receiving opening to a first exit port for ejecting a downstream plume of medication containing droplets toward the outlet port along a longitudinal axis of the body and a second exit port for ejecting an upstream plume of medication containing droplets toward the inlet port along the longitudinal axis, the first and second exit ports being sized to cause medication-containing droplets in the first and second plumes to evaporate before reaching an inner wall of the inspiratory path.

2. The device of claim 1, wherein the first and second exit ports are axially aligned with the longitudinal axis of the body.

3. The device of claim 1, wherein the body is composed of plastic.

4. The device of claim 2, wherein diameters of the first and second exit ports are approximately 0.4 millimeters.

5. The device of claim 1, wherein the inspiratory path includes 22 millimeter ventilator tubing.

6. A method of dispensing aerosol medication from an MDI canister into an inspiratory air stream flowing through an inspiratory path between a ventilator and an endotracheal tube, the method comprising the steps of:
   (a) connecting an MDI ventilation dispenser into the inspiratory path, the MDI ventilation dispenser including a medication nozzle associated with the inspiratory path;
   (b) inserting an outlet stem of the MDI canister into an inlet of the medication nozzle;
   (c) actuating the MDI canister to force a dose of medication-containing liquid into the medication nozzle; and
   (d) ejecting first and second streams of the medication-containing liquid from the MDI ventilation dispenser in opposite downstream and upstream directions, respectively, along a longitudinal axis of the MDI ventilation dispenser, the first and second streams expanding into a downstream plume of fast-evaporating droplets and an upstream plume of fast-evaporating droplets, respectively, to cause most droplets in the upstream and downstream plumes to evaporate before reaching the inner walls of the inspiratory path and thereby release dry medication particles into the inspiratory air stream.

* * * * *